(12) United States Patent
Gelardi, Sr.

(10) Patent No.: US 11,154,328 B1
(45) Date of Patent: Oct. 26, 2021

(54) TICK REMOVAL AND CAPTURE TOOL

(71) Applicant: Anthony L. Gelardi, Sr., Cape Elizabeth, ME (US)

(72) Inventor: Anthony L. Gelardi, Sr., Cape Elizabeth, ME (US)

( * ) Notice: Subject to any disclaimer, the term of this patent is extended or adjusted under 35 U.S.C. 154(b) by 511 days.

(21) Appl. No.: 15/942,854

(22) Filed: Apr. 2, 2018

Related U.S. Application Data

(60) Provisional application No. 62/480,678, filed on Apr. 3, 2017.

(51) Int. Cl.
*A61B 17/50* (2006.01)
*A01M 3/00* (2006.01)

(52) U.S. Cl.
CPC .............. *A61B 17/50* (2013.01); *A01M 3/00* (2013.01); *A61B 2017/505* (2013.01)

(58) Field of Classification Search
CPC ...................................................... A61B 17/50
See application file for complete search history.

(56) References Cited

U.S. PATENT DOCUMENTS

| | | | | |
|---|---|---|---|---|
| 1,701,995 A | * | 2/1929 | Anderson | A61B 17/30 606/210 |
| 2,461,639 A | * | 2/1949 | Grigalunas | B25B 13/48 81/176.15 |
| 3,060,442 A | * | 10/1962 | Tomek | B25C 3/008 81/44 |
| 4,020,846 A | * | 5/1977 | Stokes | A61B 17/30 606/131 |
| 4,535,538 A | * | 8/1985 | Nelson | A47G 21/02 30/147 |
| 4,938,764 A | * | 7/1990 | Glaberson | A61B 17/50 254/18 |
| 4,939,959 A | * | 7/1990 | Rokita | B25B 23/101 81/13 |
| 4,976,718 A | * | 12/1990 | Daniell | A61B 17/30 294/902 |
| 5,116,347 A | * | 5/1992 | Butler | A61B 17/50 606/131 |
| 5,374,274 A | | 12/1994 | Sproviero | |
| 5,380,339 A | * | 1/1995 | Webster | A61B 17/50 606/131 |

(Continued)

FOREIGN PATENT DOCUMENTS

WO   2016015702 A2   2/2016

*Primary Examiner* — Julie A Szpira
(74) *Attorney, Agent, or Firm* — James Creighton Wray

(57) ABSTRACT

A tick removal medical tool has an arcuate scoop with a converging V-shaped groove that moves in under the rear of the tick. Upward and outward sloping edges of the groove gently lift a tick's abdomen, legs, thorax, head and mouthpieces in that order without squeezing or decapitating the tick. A compartment in a handle holds a removable live tick trap with a hinged front door. An arcuate edge of the door matches the arcuate scoop and sweeps the live tick into the trap. A thick concave urger at the door edge centers, lifts and sweeps the tick. A probe extending forward below the urger engages and lifts the tick as the probe is raised by the upward and outward sloping surfaces of the groove. The hollow handle holds supplies or receives an extended live trap with inward sloped exit preventors imprisoning multiple live ticks for analysis.

17 Claims, 19 Drawing Sheets

(56) References Cited

U.S. PATENT DOCUMENTS

| | | | | |
|---|---|---|---|---|
| 5,554,161 | A * | 9/1996 | Thibeault | A61B 17/50 30/324 |
| 5,595,569 | A * | 1/1997 | Hebbard | A61B 17/50 606/131 |
| D388,859 | S * | 1/1998 | Carroll, Jr. | D22/122 |
| 5,843,094 | A * | 12/1998 | Saylor | A61B 17/50 606/131 |
| 6,100,501 | A * | 8/2000 | von der Heyde | A61B 17/50 219/220 |
| 6,106,041 | A | 8/2000 | Eckhardt | |
| 6,179,847 | B1 | 1/2001 | Possum | |
| 6,206,892 | B1 * | 3/2001 | Schick | A61B 17/50 606/131 |
| 6,413,266 | B1 * | 7/2002 | Mason | A61B 17/50 606/131 |
| 7,410,058 | B2 | 8/2008 | Kirkegaard | |
| 7,699,869 | B2 | 4/2010 | Meinhold | |
| 8,123,761 | B2 | 2/2012 | Herweijer | |
| 8,366,722 | B2 | 2/2013 | Herweijer | |
| 8,790,354 | B2 | 7/2014 | Makosky | |
| 8,844,193 | B2 | 9/2014 | Luongo | |
| 10,624,673 | B2 * | 4/2020 | Farnsworth | A01M 1/223 |
| 2006/0271069 | A1 * | 11/2006 | Glaesel | A61B 17/50 606/131 |
| 2008/0243181 | A1 * | 10/2008 | Schneider | F21V 33/0084 606/211 |
| 2011/0009881 | A1 * | 1/2011 | Pabari | A61B 17/50 606/131 |
| 2011/0224690 | A1 * | 9/2011 | Henson | A61B 17/50 606/131 |
| 2011/0301617 | A1 | 12/2011 | Bach | |
| 2014/0236179 | A1 | 8/2014 | Henson, Jr. | |
| 2016/0278811 | A1 * | 9/2016 | Farnsworth | A01M 3/00 |

* cited by examiner

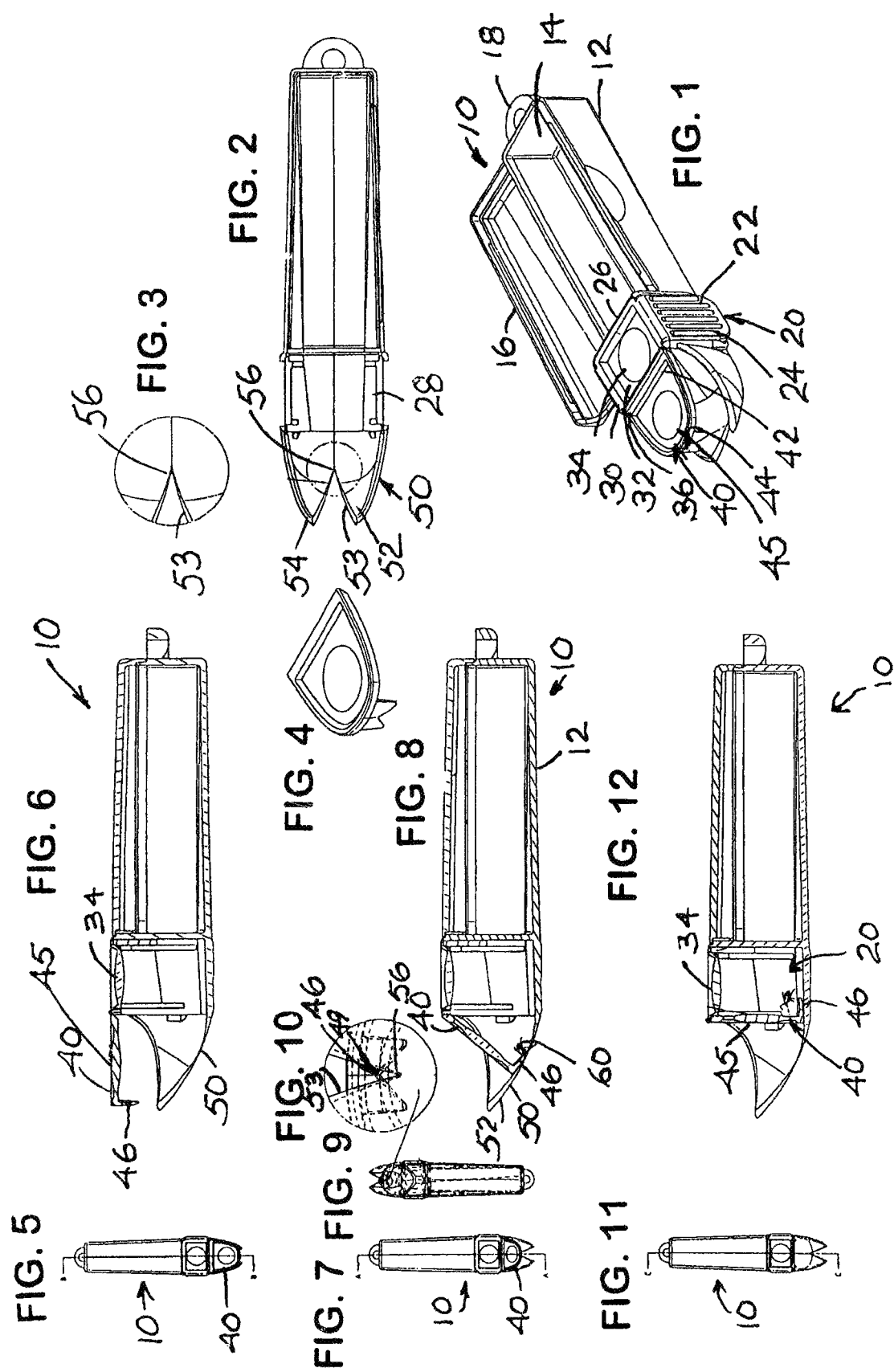

TICK REMOVAL AND CAPTURE TOOL

This application claims the benefit of U.S. Provisional Application No. 62/480,678 filed Apr. 3, 2017, which is hereby incorporated by reference in its entirety as if fully set forth herein.

BACKGROUND OF THE INVENTION

Ticks carry diseases. Particular species of ticks are more likely to carry particularly dangerous diseases. Ticks have three mouth parts extending from a head. One of the mouth parts is a hypostome, a knife with barbs that resist withdrawal. The barbed knife-like part has a groove that carries saliva into a host and carries blood out. Two other mouth parts are sharp-pointed chelicerae which work to pull the hypostome into the host until the head is pulled tight against the host's skin. The tick's body fills with blood and swells.

A tick can bite without pain and remain attached for hours or days. If the body is squeezed, blood and saliva flows back into the host. It is important to lift the tick and its head from the skin without squeezing the tick. It is also necessary to see the tick when lifting it and to lift the head to pull the mouth parts from the skin. It is important to capture the tick and to observe the captured tick to try to identify its species.

It is important to capture the tick alive and to observe the captured tick by the removing person or test laboratory to try to evaluate its species.

Other devices for removal of ticks from the skin kill the tick by drowning in fluids like baby oil, burned by heat, crushed by improper removal, electrocuted or frozen, all damaging or killing the tick, making it difficult or impossible to identify the species. Test laboratories teach live ticks are the preferred form for accurate identification.

The invention solves problems of pulling the complete tick from a body, seeing the tick as it is pulled, and capturing for observing the captured tick.

SUMMARY OF THE INVENTION

The invention is an all-inclusive medical device that includes means to locate, position, remove, sweep, capture, observe, identify, store, submit for testing, or dispose of a tick in a removable and replaceable locked container, without any secondary requirements that may include touching or handling a loose tick by a removing person.

The invention is an all-inclusive medical device for antiseptically removing parasitic ticks from both humans and animals. The device has a handle on an arcuate scoop with a tapered centered slot that assists in positioning the tick for removal. The hinged door attached to a trap, includes a compliant nudging member, and when closed, nudges and separates the tick from the skin and sweeps it into a now locked trap that is removable and can be held, tested, or disposed. There are no secondary operations needed.

An integral magnifying lens in the hinged trap door is positioned above the scoop allows observation of the tick for correct positioning in the scoop's slot. A compliant finger-like nudger attached to the center of the hinged trap door, when closing, arcs along the "v" notch contacting the tick-attaching mouth part and nudges, detaches and sweeps it into a trap that is now locked. a second magnifying lens can be included in the top of the trap helps in identifying the type of tick lodged in the trap. The removable trap may have an extension that fits into all or part of the handle storage space. The trap extension has a natural sticky glue coating along all of the internal walls of the trap. This configuration is designed for animals and the capture of dozens of ticks within each trap. The trap extension includes a funnel like opening with the smallest opening facing inwardly that does not allow for personal contact with the interior. The trap with extension is designed to capture and terminate ticks not for testing.

A handle, which is attached to the scoop and retains the trap assembly, includes a compartment for holding supplies like antiseptic wipes, bandages and other tick related information. A loop for attaching the device to a belt, backpack, collar, leash, or key chain is provided on the end of the handle. A printed sleeve or label fits over the handle identifies species of relevant ticks and sizes and can be used to compare with the captured tick in the removable trap. The invention is an all-in-one medical device that includes means to locate, position, remove, sweep, capture, observe, identify, store, submit for testing, or dispose without any secondary requirements that may include touching or handling a loose tick by the removing person.

A strap attached to the trap door allows for the trap to be opened after removal from the device. An extended strap is design to allow the trap for animals to be opened without removing from the device.

The invention is an all-inclusive tool for antiseptically removing ticks from both animals and humans. A handle on an arcuate scoop with a tapered slot assists in positioning the tick. A hinged sweeper cooperates with the scoop for lifting the tick's body and head for removal. A magnifying lens in the hinged sweeper above the scoop allows observation of the tick for correct placement in the scoop's slot. A fork on an edge of the hinged sweeper moves along the scoop, capturing and pulling the tick's head, and locks the tick into a closed trap. A second magnifying lens above the trap helps in identifying the type of tick lodged in the trap. A handle, which is attached to the scoop and trap assembly, includes a compartment for holding supplies. A loop for attaching the tool to a belt, backpack or key chain is provided on the end of the handle. A printed sleeve fits on the handle, identifies ticks and sizes and compares them with one or more ticks in the trap.

The invention is an all-in-one device that includes a means to locate, remove, capture, withdraw, observe, identify and store a tick without any contact between the tick and a removing person.

The invention includes a tick remover and trap having a tick scoop.

A V-shape notch in the scoop is wide at the front of the scoop and narrowing toward the center of the scoop.

A handle is connected to the back of the scoop. A compartment is in the handle at the back of the scoop. A trap is positionable in the compartment for retaining one or more removed ticks. The trap has a top, sides, a bottom, a back and a front. A door has a top, sides and a bottom and a hinge connecting the top of the door and to the trap.

The top of the door is connected to the trap near an intersection of the top and the front of the trap. The bottom of the door contacts the bottom of the scoop near the narrowing of the V-shaped notch for urging a tick toward the front of the trap. The scoop is curved and the bottom of the door is curved to sweep along the curved scoop to lift a tick, its legs and mouth parts from skin and to move a tick toward the trap.

Lower portions of the scoop sides are curved inward toward the curved bottom of the door to sweep a tick toward the trap.

The front of the trap is open to receive one or more ticks removed by the scoop and the door.

The door closes the open front of the trap. The door is held closed on the front of the trap by friction or cooperating snaps. The door has extensions on the back of the door extending from the sides and the bottom of the door for sweeping the scoop and urging a tick toward the trap.

The V-shaped notch has upward sloping edges for lifting a tick as the scoop relatively moved under a tick. The door has a nudger extending rearward from a center of the bottom of the door. The nudger is V-shaped, narrowing inward toward a center of the nudger.

A flexible finger extends below and forward of the nudger toward the trap. The flexible finger has flat lower surfaces and a depending middle projection. The flat lower surfaces engage the upward sloping edges of the V-shaped notch, and the depending middle projection rides in the V-shaped notch until the sloping side edges near an apex of the V-shaped notch lift the flexible finger, which in turn gently lifts the tick, its head and rostrum proboscis from skin.

The handle has a hollow body and has a longitudinally hinged lid connected to the hollow body. The hollow body is used for storage of auxiliary devices.

In one form, the trap is longitudinally extended, has longitudinally extended walls and extends into the hollow body beneath the lid. The trap includes angular inward and rearward extending barriers extending into the trap from longitudinal walls spaced slightly inward from the front of the trap adapted for preventing live ticks held deep in the trap from crawling outward beyond the barriers toward the front of the trap.

The new invention urges ticks outward from skin by engaging a tick from its rear and lifting legs of a tick onto a scoop, urging the tick along a V-shaped notch narrowing inwardly in the scoop, gently lifting the scoop and notch by moving the handle downward, following the tick inward along the scoop and into an open front end of a trap with a door hinged to a top of the trap, and capturing the tick in the trap by closing the door over the front end of the trap.

The method of the invention further includes nudging the tick away from the skin with upwardly sloping side edges of the V-shaped notch and with a nudger extending inwardly toward the trap along a bottom edge of the door. The new method further includes urging a tick upward from skin with the flexible finger extending forwardly from a bottom of the nudger.

Raising the flexible finger with the upwardly sloping side edges of the V-shaped notch lifts the tick head. The flexible finger is configured for gently lifting a head and rostrum proboscis of a tick from skin.

The method further includes rotating the scoop and trap upward and shaking a freed tick to a back of an elongated trap beyond inward sloping tick return-preventing extensions near the front of the trap.

These and further and other objects and features of the invention are apparent in the disclosure, which includes the above and ongoing written specification, with the claims and the drawings.

BRIEF DESCRIPTION OF THE DRAWINGS

FIG. 1 is a perspective view of the tick removal and capture tool.

FIG. 2 is a bottom view of the tool showing the V-slot in the removal scoop.

FIG. 3 is a bottom view enlarged detail of the removal scoop.

FIG. 4 is a perspective detail of the sweeper that is hinged on the trap of the removal tool.

FIGS. 5 and 6 are a plan view and a vertical cross-sectional view of the tick removal and capture tool showing the sweeper and fork in a home position before the tool is used.

FIGS. 7 and 8 are a plan view and a vertical cross-sectional view of the tick removal and capture tool, showing the sweeper at about a 54° downward rotation after the scoop has been pressed downward and slid under a tick. The removal of the tick begins by engaging the tick under its body and head in the cooperating apexes of the scoop and sweeper. The scoop, sweeper and fork hold the tick while it is lifted from the skin.

FIGS. 9 and 10 are a bottom view and a detail showing apexes of the scoop and sweeper as they are moved together under the tick.

FIGS. 11 and 12 are a plan view and a vertical cross-sectional view of the tick removal and capture tool showing the sweeper and fork in the locked position.

DETAILED DESCRIPTION

Figure 13:
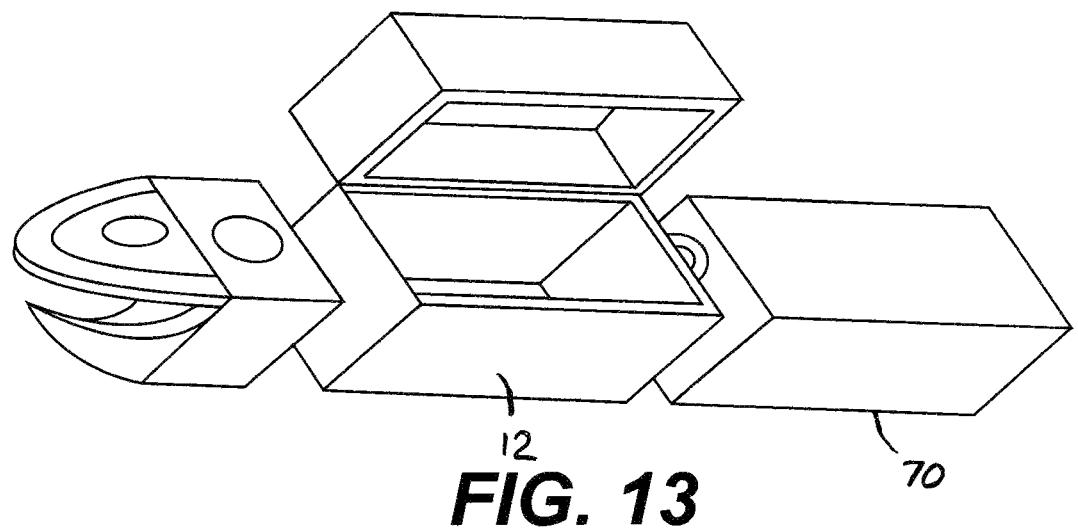
FIG. 13 shows a sleeve for sliding on the handle after its lid is closed.

FIG. 1 shows the tick removal and capture tool 10. FIG. 2 shows the V-slot in the removal scoop 50. FIG. 3 is a detail of the removal scoop 50. FIG. 4 is a detail of the sweeper 40 that is hinged on the removal tool 10. The tool 10 has a handle 12 with a compartment 14 and a lid 16 for holding objects such as narrow-jawed tweezers and other items that may be useful on a walk or hike. A loop 18 at the end of handle 12 is useful to attach to a line, hook, chain or caribiner. The front of handle 12 is connected to the trap 20. The trap has ridges 22 on its sides 24 to provide secure finger and thumb gripping areas. An end 26 of the trap near the handle 12 is closed by a wall. The bottom 28 of the trap is also closed. The top 30 of the trap 20 has a wall 32 holding an integrally formed magnifying lens 34 for viewing a tick captured within the trap and observing features of the tick which may be indicative of its species.

A living hinge 36 at a front of top 30 connects to a sweeper 40. The generally planar sweeper has a straight rear edge 42 which is attached to the living hinge 36. A curvilinear free edge 44 surrounds the front and sides of the sweeper. A wall 45 inside the raised edges 44 has an integrally molded magnifying lens 45. Lens 45 allows observation of the tick and the tick's body, legs and head as parts of the tool 10 are being arranged around a tick. A sweeper fork 46 extends downward around a tick from the front of the sweeper 40. The sweeper fork has triangular teeth separated by an inward converging triangular gap 48 with an apex 49.

The front tick removal part of tool 10 has a curvilinear scoop 50. Scoop 50 has two forward and upward curving sections 52 and 54 which are spaced apart by a generally triangular V-slot 53. The slot 53 terminates inwardly in an apex 56. The curvilinear scoop 50 has a complex curved surface curved around a longitudinal radius and around a radius from a center of the living hinge 36. Curved sides of the scoop 50 are constructed to closely cooperate with the curved edge 44 of the sweeper 40 to capture and trap a targeted tick.

FIGS. 5 and 6 are a plan view and a vertical cross-sectional view of the tick removal and capture tool 10 showing the sweeper 40 and fork 46 in a raised home position before the tool is used. The trap 20 is open while the sweeper 40 is raised. Lens 34 in trap 20 and lens 45 in the sweeper are shown in the cross-section. The curvature of scoop 50 is also shown.

FIGS. 7 and 8 are a plan view and a vertical cross-sectional view of the tick removal and capture tool 10 showing the sweeper 40 and fork 46 at about a 54° downward rotation after the scoop has been rotated and pressed downward under a tick to begin the removal of the tick by engaging the tick under its body and head in the cooperating apexes of the scoop and sweeper before engaging the tick under its head. The sweeper 40 is shown in the partially downward position. A tick 60 has been located. The scoop 50 of the tool 10 has been manipulated with the handle 12 so that the scoop is pressed downward on the skin around the place where the tick is attached. Using the handle to slide and rotate the spaced curving sections 52 under the tick, the tick is positioned in or near the apex 56 of the V-slot 53 between the curved sections of the scoop. The sweeper 40 has been rotated downward so that the fork 46 engages the tick near the apex 56 of the sweeper's V-slot.

FIGS. 9 and 10 are a bottom view and a detail showing apex 56 of the scoop 50 and apex 46 of sweeper 40 as they are moved together under the tick and its head. FIGS. 9 and 10 show the relative position of the sweeper's converging gap 48 and its apex 49 with respect to the apex 56 of the triangular slot 53 in the scoop 50 when the tick is ready to be lifted from the skin.

FIGS. 11 and 12 are a plan view and a vertical cross-sectional view of the tick removal and capture tool 10 showing the sweeper 40 and fork 46 in the locked position as the front of trap 20.

FIGS. 11 and 12 show the position of the sweeper 40 when it is locked in the down position to hold the tick in trap 20. The lens 34 in the top 30 of trap 20 and the lens 45 in sweeper 40 are used to view and identify, if possible, the tick held in the trap.

As shown in FIG. 13, the handle 12 may be encased in a slidable sleeve 70 with graphics helping to identify the tick.

The trap may be detachable from the handle. The trap with the hinged and locked sweeper may be separated from the handle and separately stored with the captured tick. A replacement trap with an attached hinged sweeper may replace the separated trap.

Each detachable and replaceable trap has a top, bottom, rear and side walls. A sweeper is hinged to the front of top. Side walls of the replaceable traps fit inside side walls extending forward from the handle. Bottom of the replaceable trap fits inside a forward extending bottom that is attached to the handle and to the side walls extending forward from the handle.

L-shaped locks extend inward from side walls to fix the trap in place until it is intentionally removed after capturing a tick. The scoop is attached to the bottom and side walls of the tool.

Figure 14:
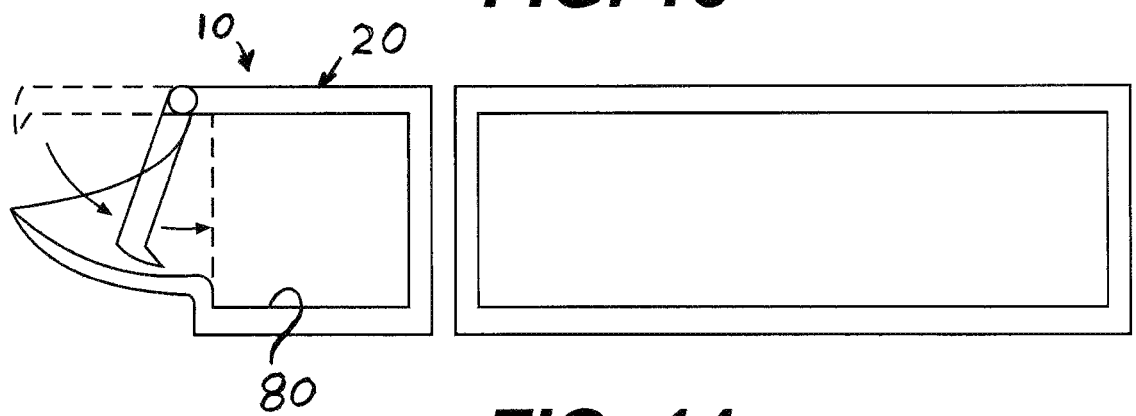
FIG. 14 shows a trap with a dropped bottom to hold a tick while another tick removed from skin is swept into the trap.

As shown in FIG. 14, the tool 10 may have a trap 20 with a depressed bottom 80 that holds a tick and prevents it from crawling out of an open trap when tool 10, sweeper 40 and scoop 50 are used to lift and sweep another tick into the trap.

Figure 15:
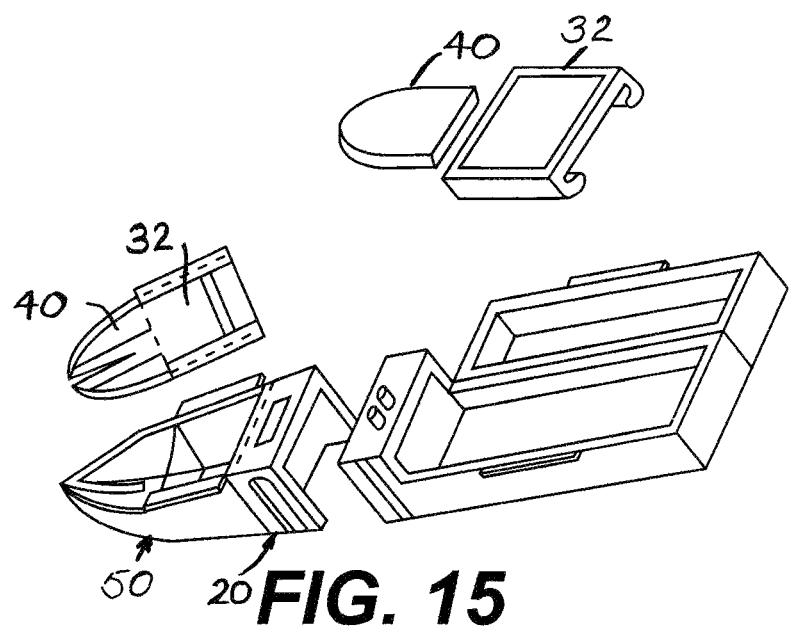
FIG. 15 schematically shows molded parts for assembling into the tool.

As shown in FIG. 15, the tool 10 may be molded in parts. The handle 12, the trap top 32 and the sweeper 40, and the front of the trap 20 and scoop 50, may be molded as separate units.

FIGS. 16-23 are views and details of an embodiment of a tool 100 with an insertable and removable trap 120 having an attached sweeping and locking door 140 attached by a living hinge 136.

Figure 16:
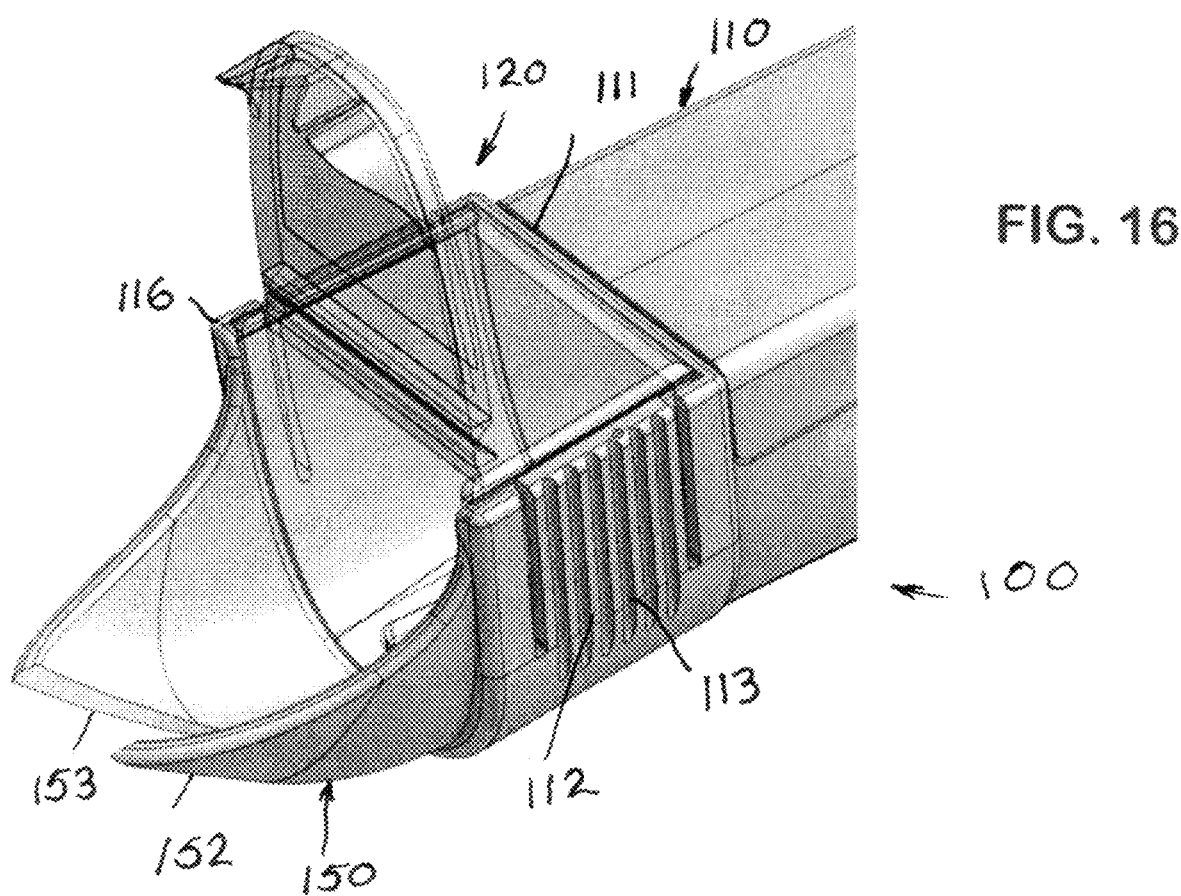
FIG. 16 is a perspective detail showing a removable trap seated and locked in a holder between a handle and a scoop.

FIG. 16 shows the trap 120 nested in a holder 111 which extends forward from a handle 110. A holder has sides 112 with grooves 113 for gripping, a rounded bottom 114 and an open top 116. Curved scoop 150 extends from holder 111. Projections 152 are separated by V-slot 153.

Figure 17:
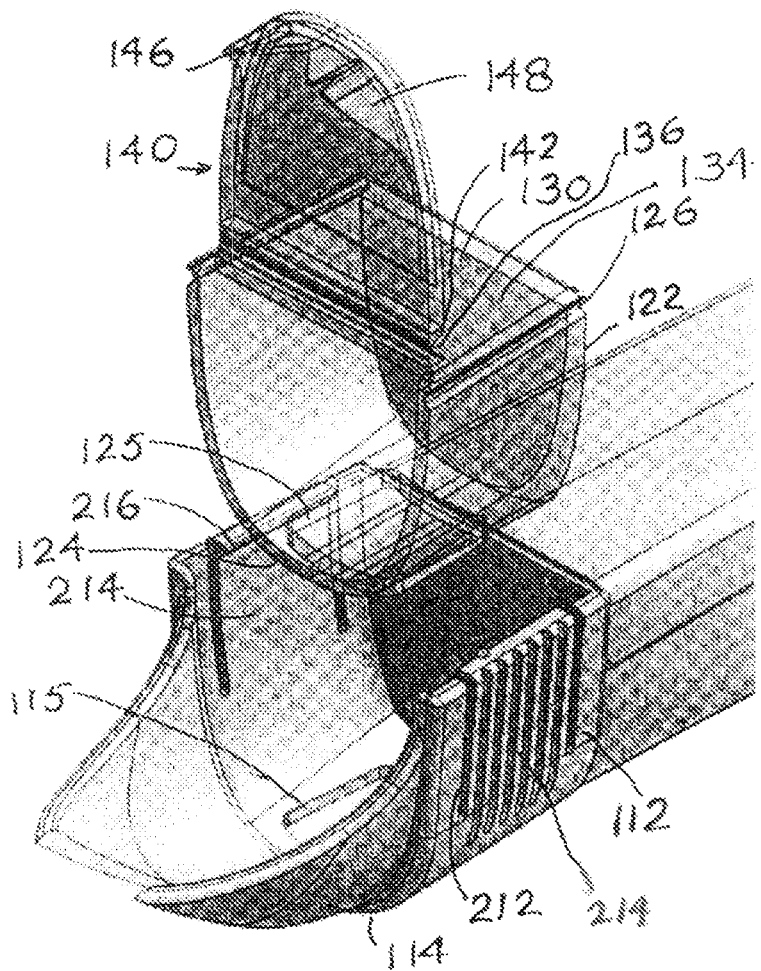
FIG. 17 is an exploded view showing the trap out of the holder.

As shown in FIG. 17, the sides 112 having openings 212 which form springs 214 for holding inward projecting retainer beads 216. The bottom has a rhomboidal-shaped opening 115 shown in FIG. 18 to stabilize a similar projection 125 on a rounded bottom 124 of removable trap 120. Rounded sides 122 of the trap terminate upwardly in grooves 126 to receive the elongated detent retainer beads 216 on side springs. A top 130 of trap 120 is flat. A back 134 completes the body of the trap and fits against the front wall of handle 110. The sweeping and locking door 140 has a back edge 142 which is joined by a living hinge 136 to the top 130 of the trap 120.

Door 140 has a fork 146 and guides 148, as shown in FIGS. 17 and 20-22.

The fork 146 and guides 148 are rounded and contact the curved inside of scoop 150 as the sweeper door 140 is rotated downward and inward around living hinge 136. The fork 146 and guides 148 aid in lifting and in preventing escape of a tick about to be swept into and captured in the trap 120. Fork 146 and guides 148 then contact the inside of rounded bottom wall 124 of the trap, holding the sweeper door 140 closed.

The entire trap 120 and attached sweeper door 140 are transparent. With a little shaking, a trapped tick can be lodged in the clear projection 125 at the bottom of the trap 120 for close viewing and identification.

Figures 22, 23:
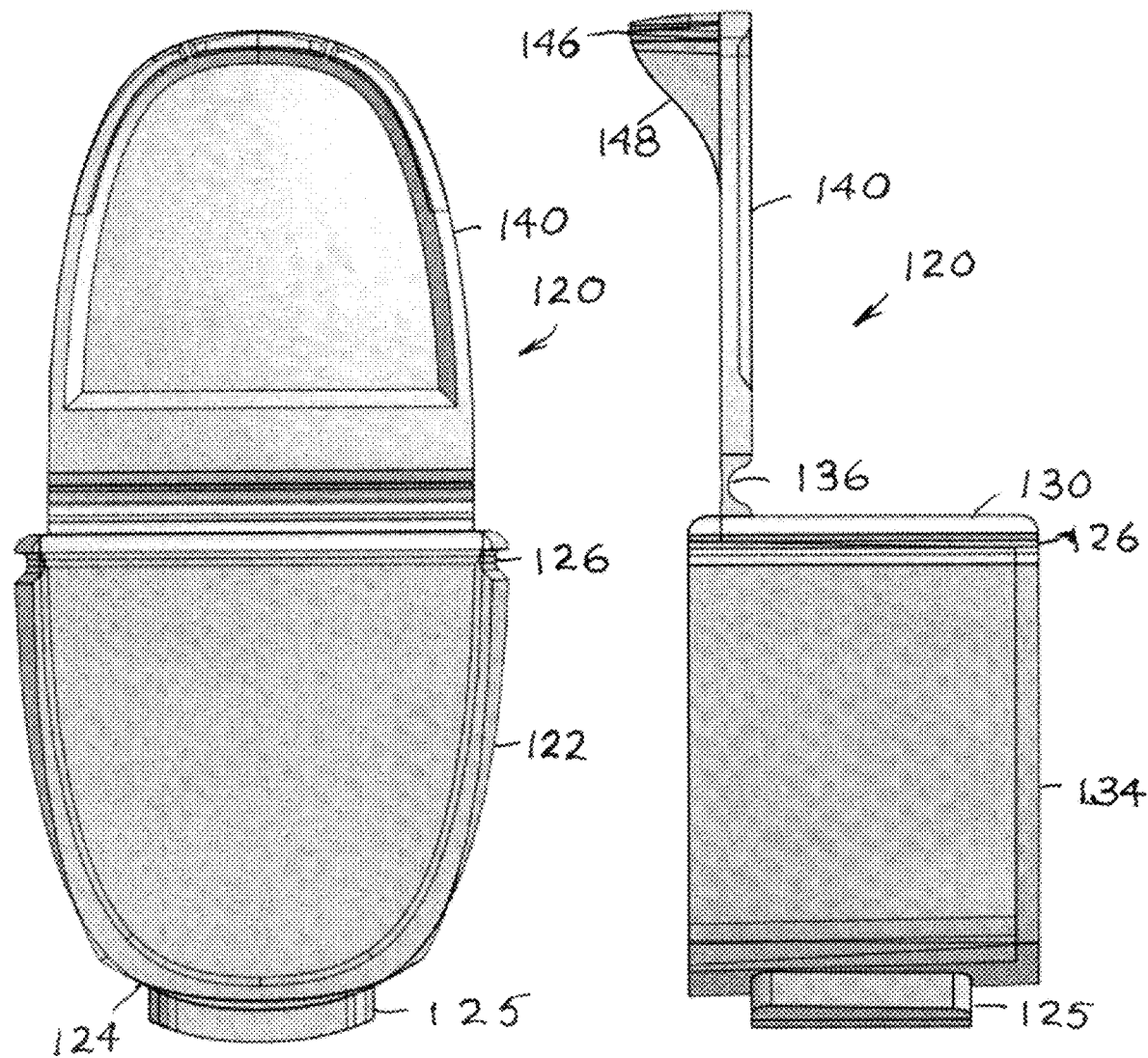

Side and rear views of the removable trap 120 and sweeper door 140 are shown in FIGS. 22 and 23.

FIG. 16 is a perspective detail showing a removable trap seated and locked in a holder between a handle and a scoop.

FIG. 17 is an exploded view showing the trap out of the holder.

Figure 18:
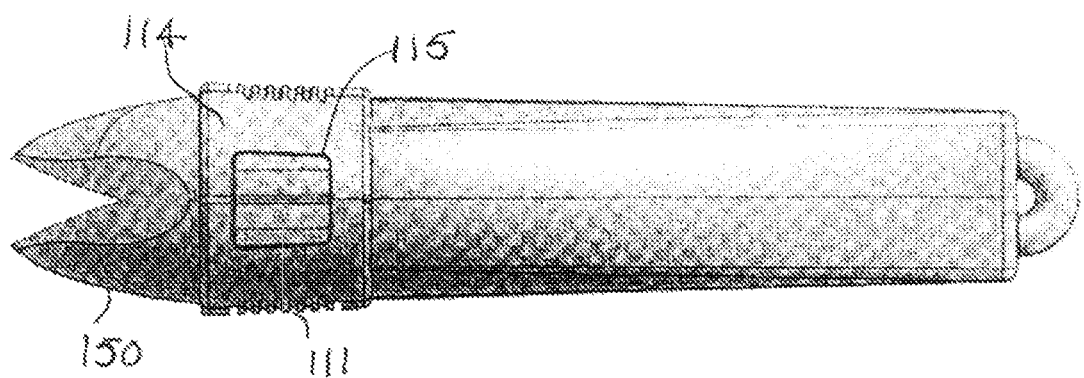
FIG. 18 is a bottom view showing a clear projection from a bottom of the trap in a similarly shaped opening in the bottom of the holder.

FIG. 18 is a bottom view showing a clear projection from a bottom of the trap in a similarly shaped opening in the bottom of the holder.

Figure 19:
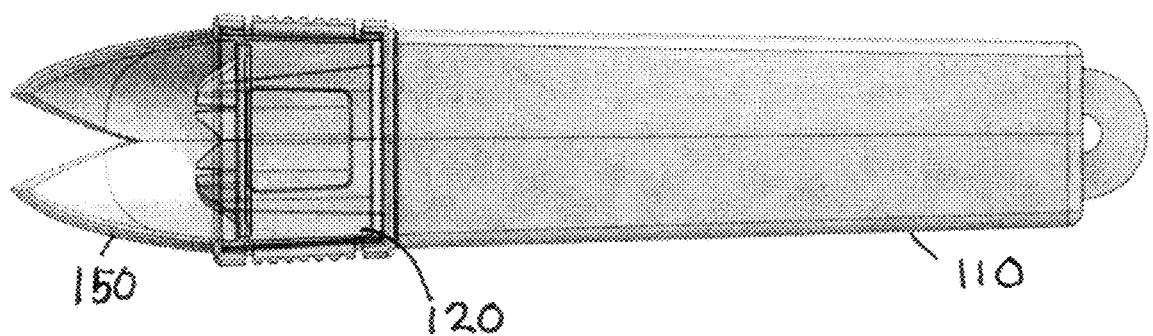
FIG. 19 is a top plan view and FIG. 20 is a side view of the tool.
Figure 20:
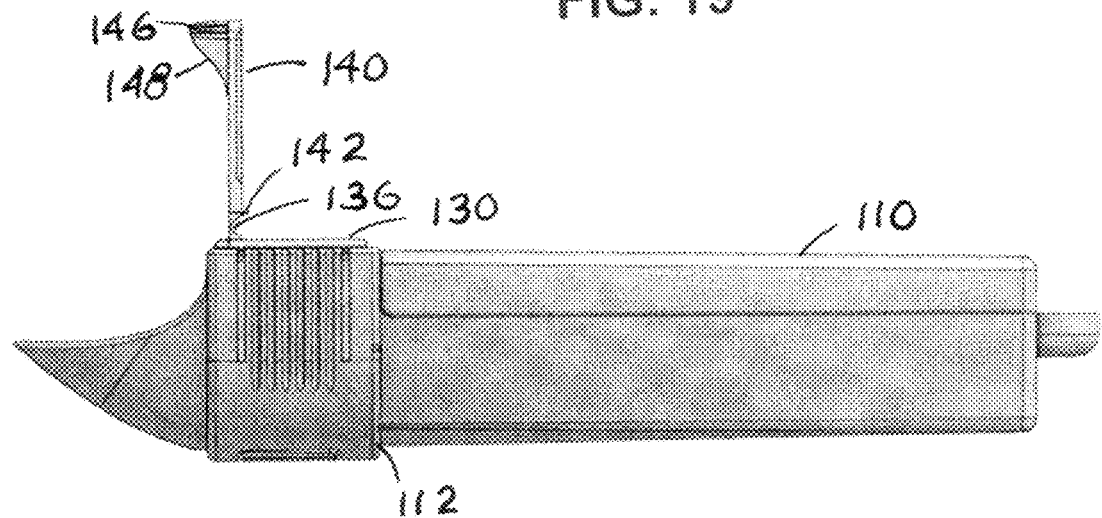

FIG. 19 is a top plan view and FIG. 20 is a side view of the tool.

Figure 21:
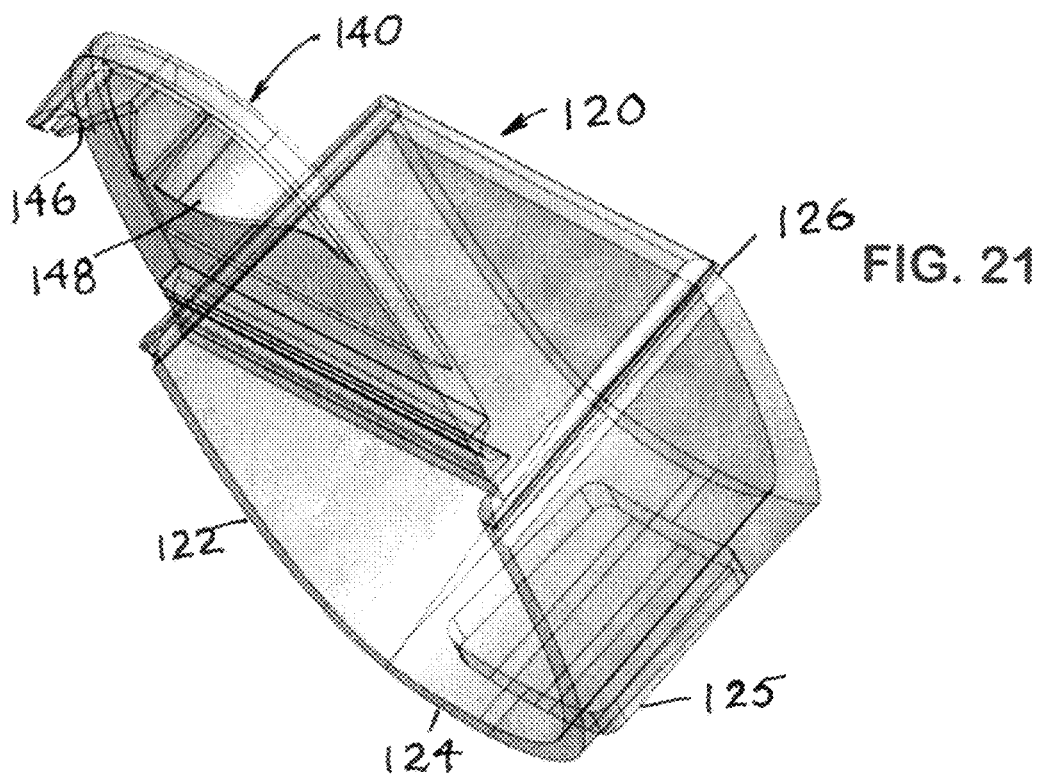
FIGS. 21, 22 and 23 are perspective, side and rear views of the removable trap.

FIGS. 21, 22 and 23 are perspective, side and rear views of the removable trap.

Figure 24:
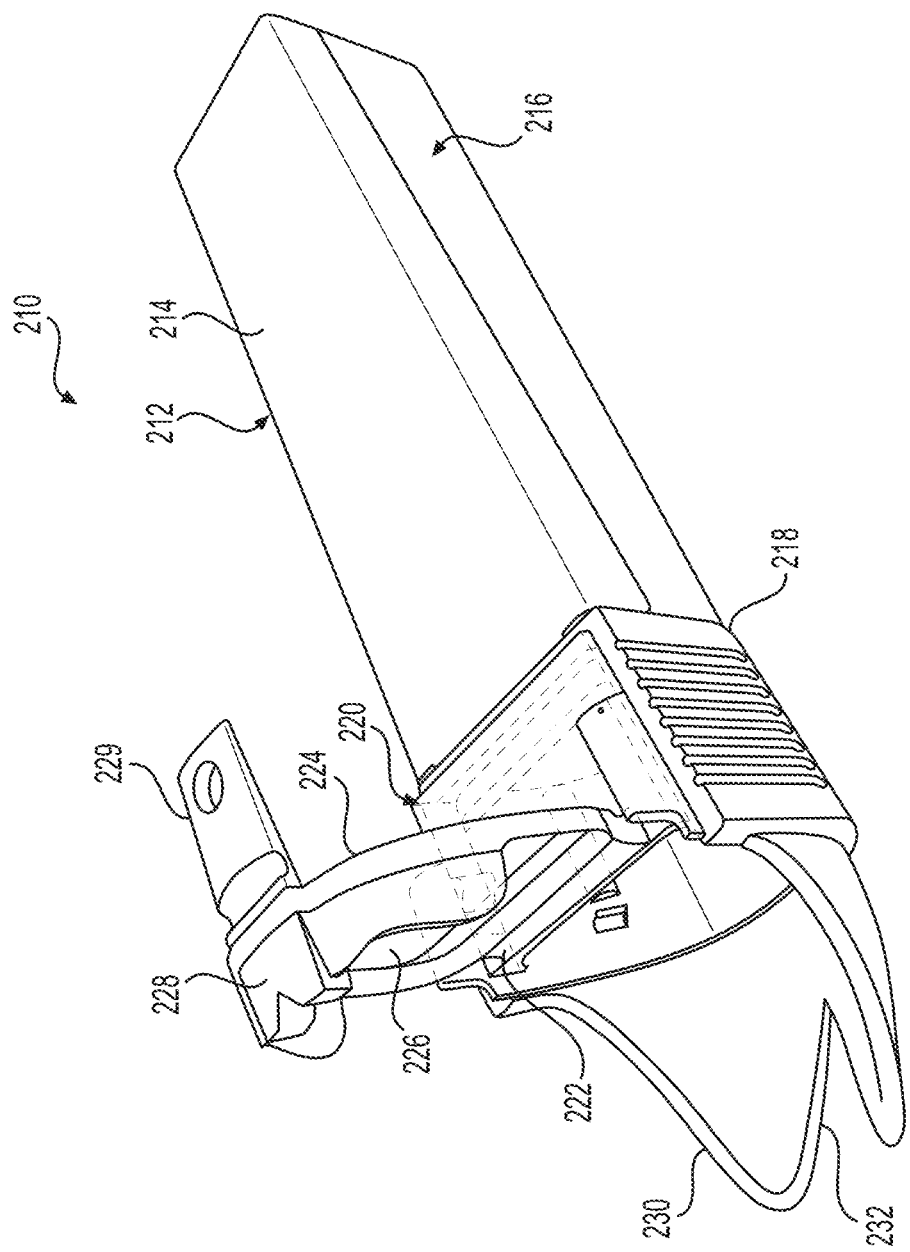
FIG. 24 shows a modified tick remover and trap.

FIG. 24 shows a modified tick remover and trap.

Figure 25:
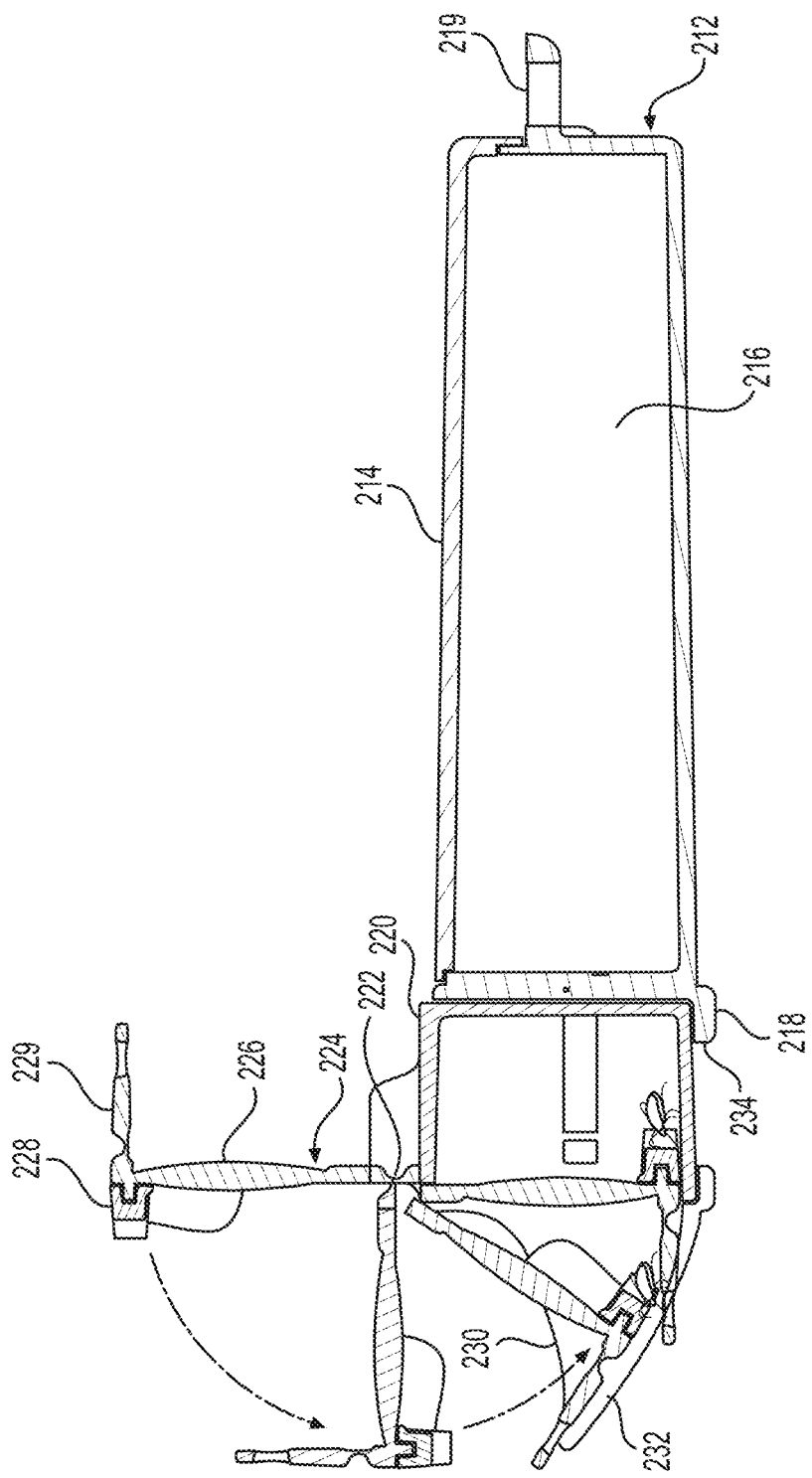
FIG. 25 is a side cross-section of the tick remover and trap.

FIG. 25 is a side cross-section of the tick remover and trap.

The tool 210 has handle 212 with a removable and replaceable trap 220. The handle 212 has a living hinge joined top 214 opening to a compartment 216 to hold bandages, antiseptic wipes and submission tags for marking and submitting the trap with its captured ticks to tick and disease identification facilities. A sleeve with instructions and graphics slides over the handle 212 to hold the top closed.

The arcuate scoop 230 that extends forward from the handle 212 has a tapered "V" slot 232 to slide under the back of a tick. A ring 219 at the back of the handle 212 attached to a belt or backpack. A living hinge 222 attaches a hinged trap door 224 to the top of the open front of the replaceable tick trap 220. The top, bottom, sides and back of the trap 220 are solid. A magnifying lens 226 is centered in the hinged trap door 224. An enlarged curved nudge 228 at the curved bottom of the trap door 224 cooperates with the arcuate scoop 230 to sweep the captured tick from the "V" slot 232 into the trap 220. The trap door 224 is held closed by friction and complementary snaps until the door is pulled open with the trap door opening strip 229 attached to the outside of the rounded bottom of the door.

A hole 234 through the bottom of the trap housing 218 in handle 231 allows the trap 220 to be pushed upward out of the housing. Grips 236 at the sides of the handle housing are held when inserting the scoop and groove 232 beneath a back of a tick.

Figure 26:
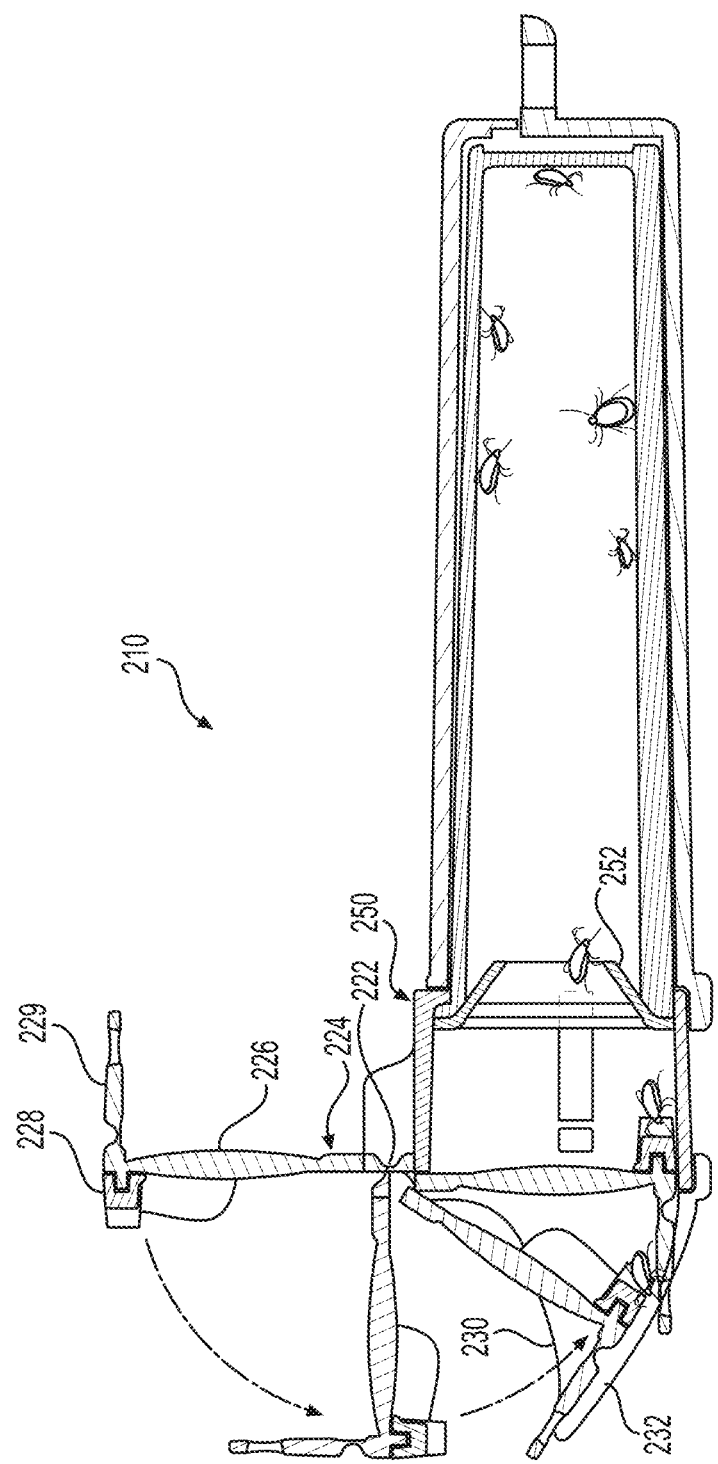
FIG. 26 shows a tick remover with an extended trap.

FIG. 26 shows a tick remover with an extended trap.

Figure 27:
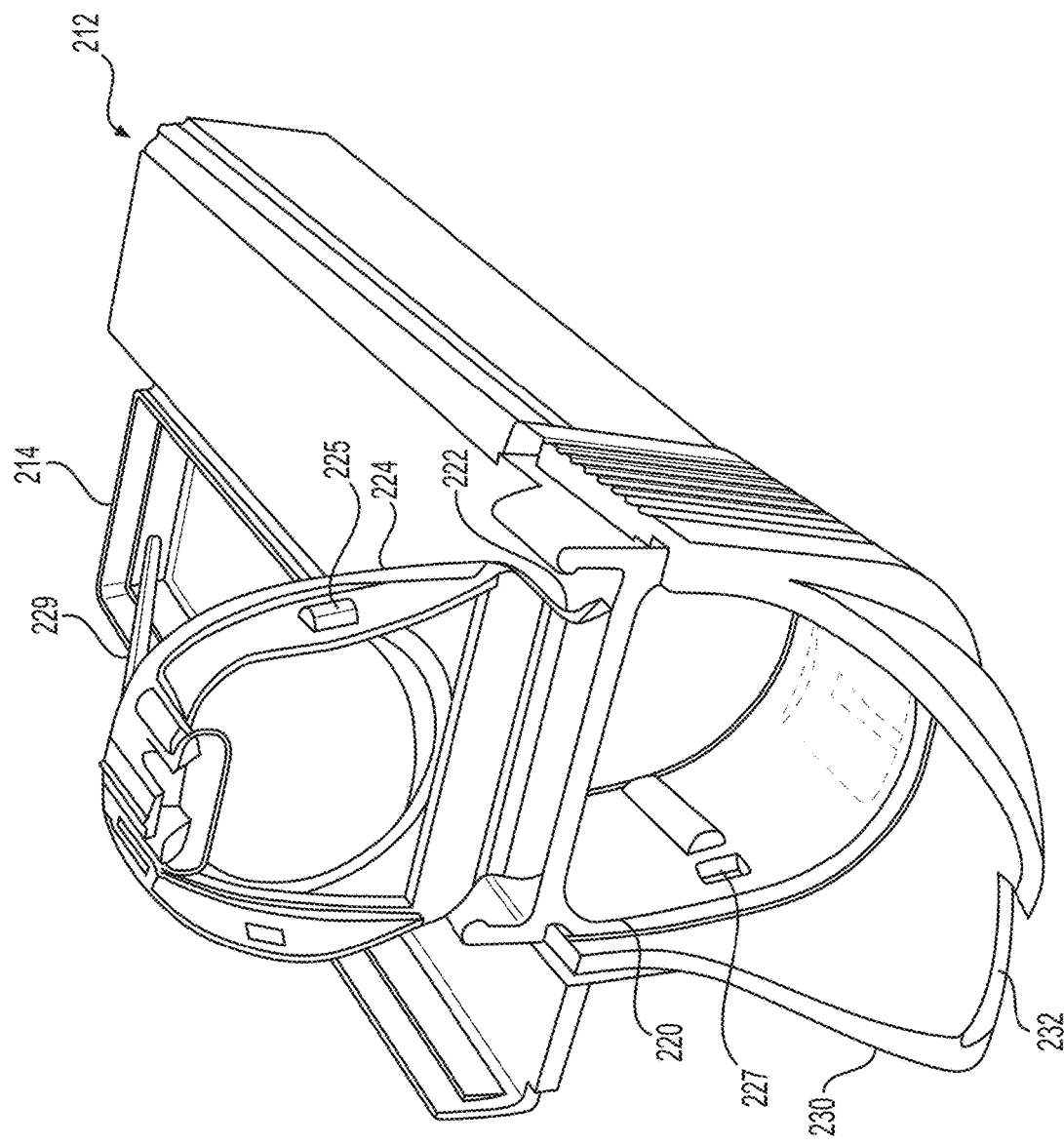
FIG. 27 is a front perspective view of the tick remover.

FIG. 27 is a front perspective view of the tick remover.

Figure 28:
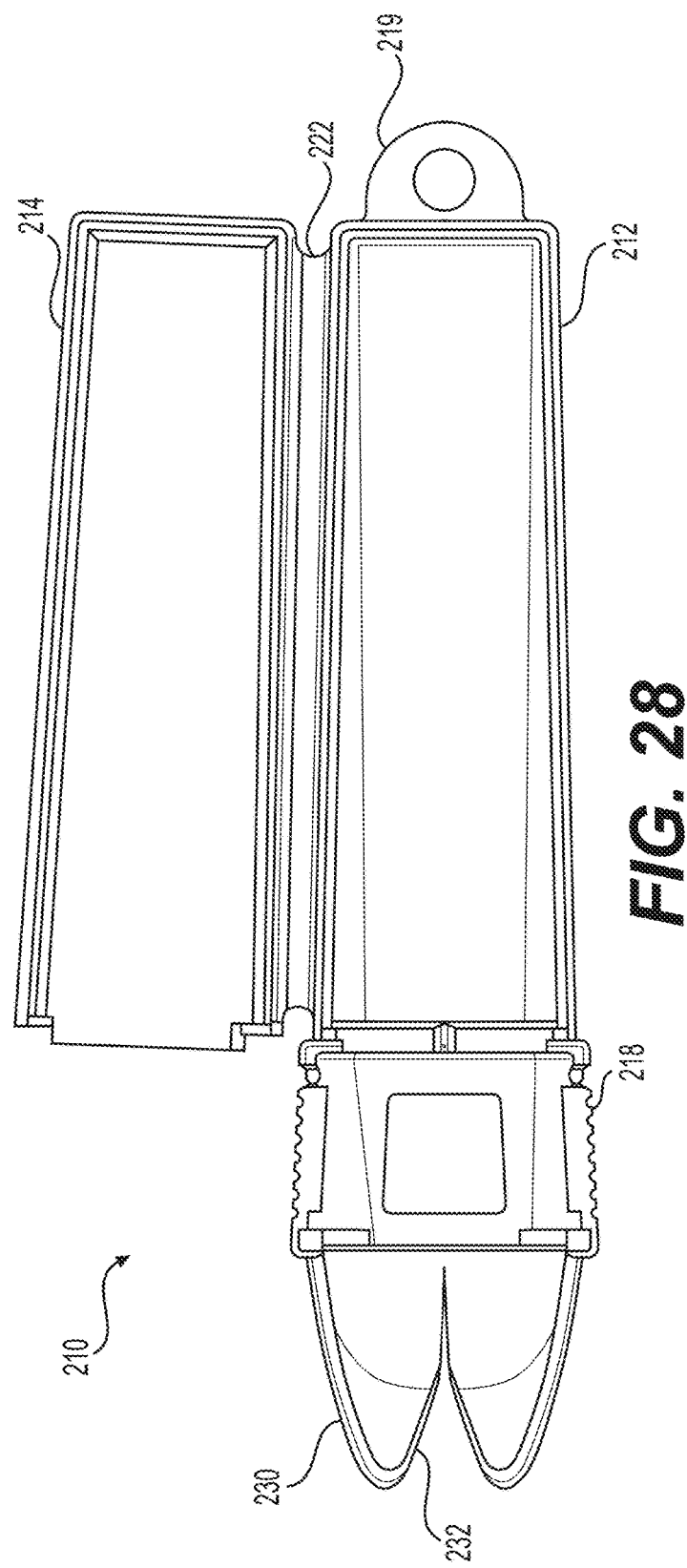
FIG. 28 is a top view of the tick remover shown in FIG. 26 with the top open and the trap removed.

FIG. 28 is a top view of the tick remover shown in FIG. 26 with the top open and the trap removed.

Figure 29:
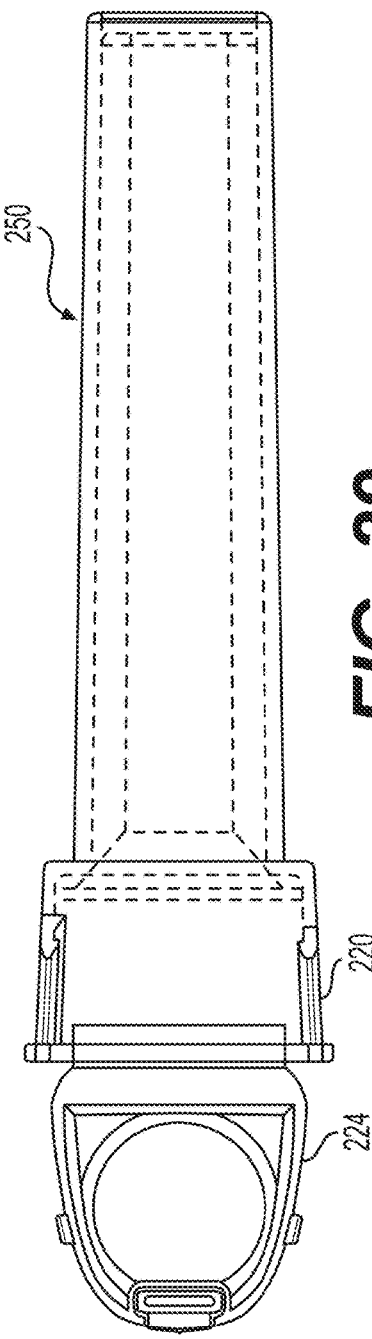
FIG. 29 is a top view of the axially elongated trap for fitting inside the holder shown in FIG. 28.

FIG. 29 is a top view of the axially elongated trap for fitting inside the holder shown in FIG. 28.

Figure 30:
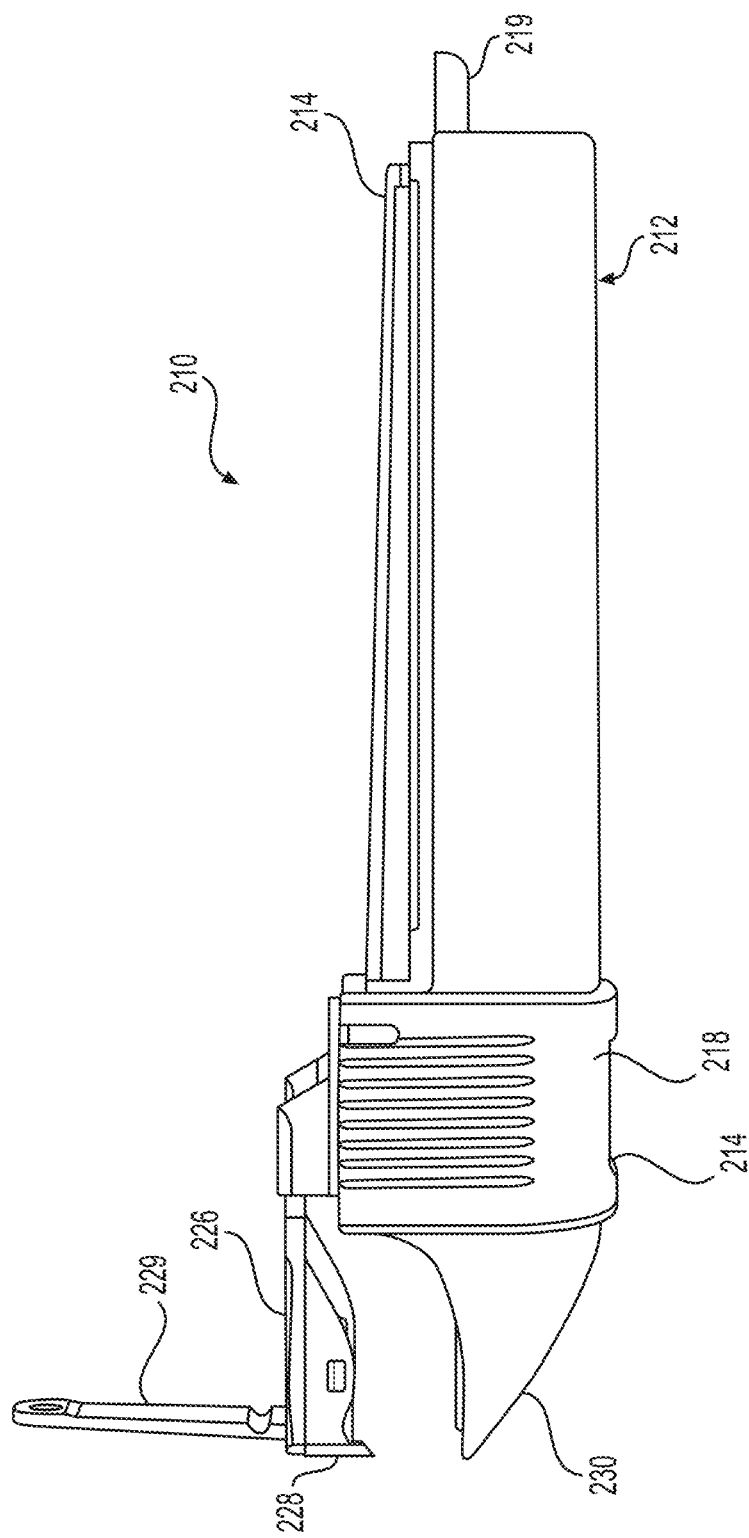
FIG. 30 is a side view of the tick remover, sweep door, finger and opening strap.

FIG. 30 is a side view of the tick remover, sweep door, finger and opening strap.

Another construction shows an elongated trap 250. The front is the same. After a tick is pushed back by the door, the tool 210 is tipped vertically and shaken to dislodge the ticks toward the back of the long trap. The sloping 252 walls, top and bottom stop the ticks from returning toward the door. Looking through the magnifying lens 226 on the door 224, one observes that the front of trap 250 is empty before pulling on the opening strip 229 to open the door for another capture. The elongated trap 250 is particularly useful when lifting multiple ticks from animals.

The door 224 has snaps 225 to cooperate with snaps 227 on the trap 220 to hold the door closed.

Figure 31:
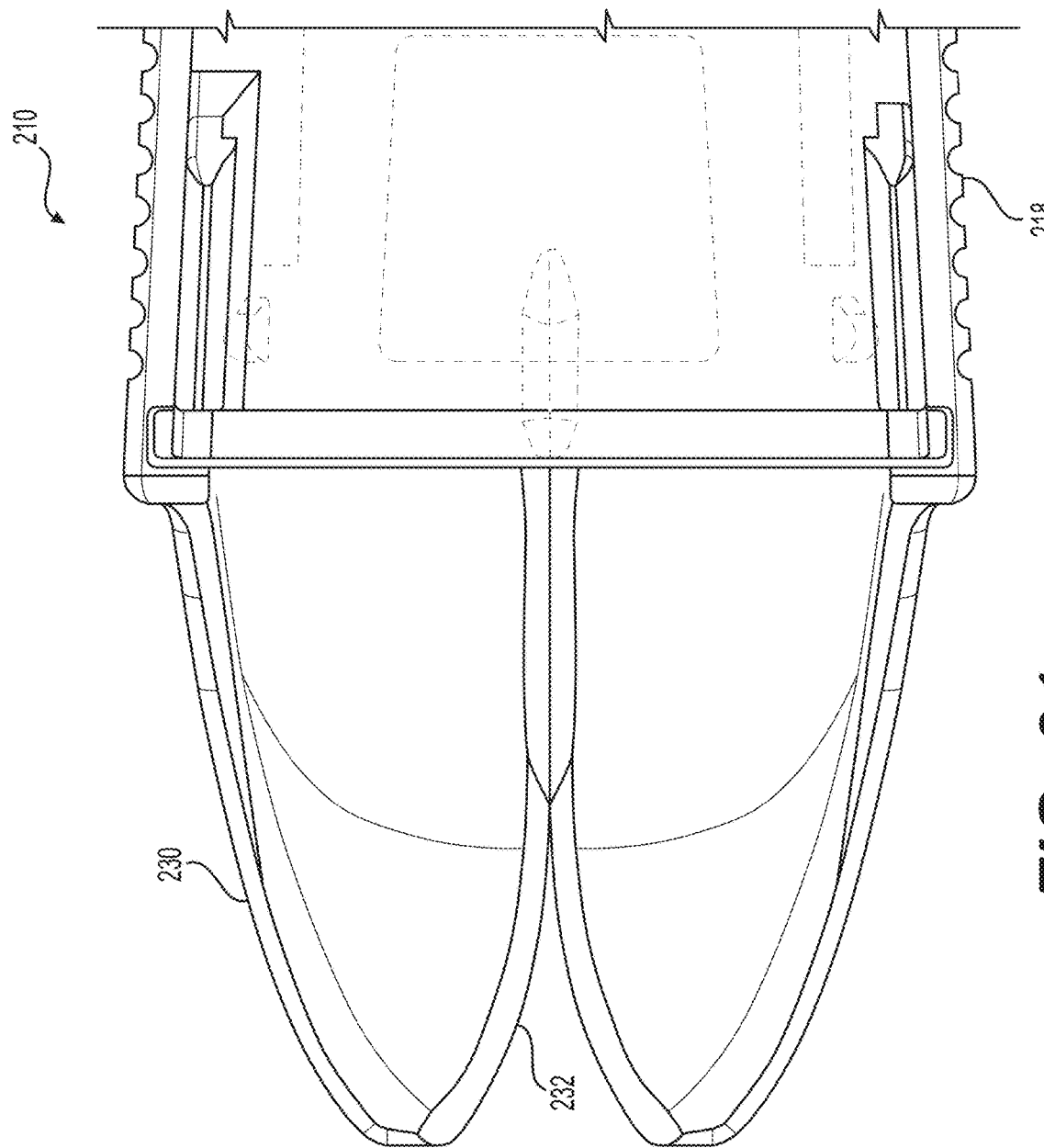
FIG. 31 is a top detail of the tick remover.

FIG. 31 is a top detail of the tick remover.

Figure 32:
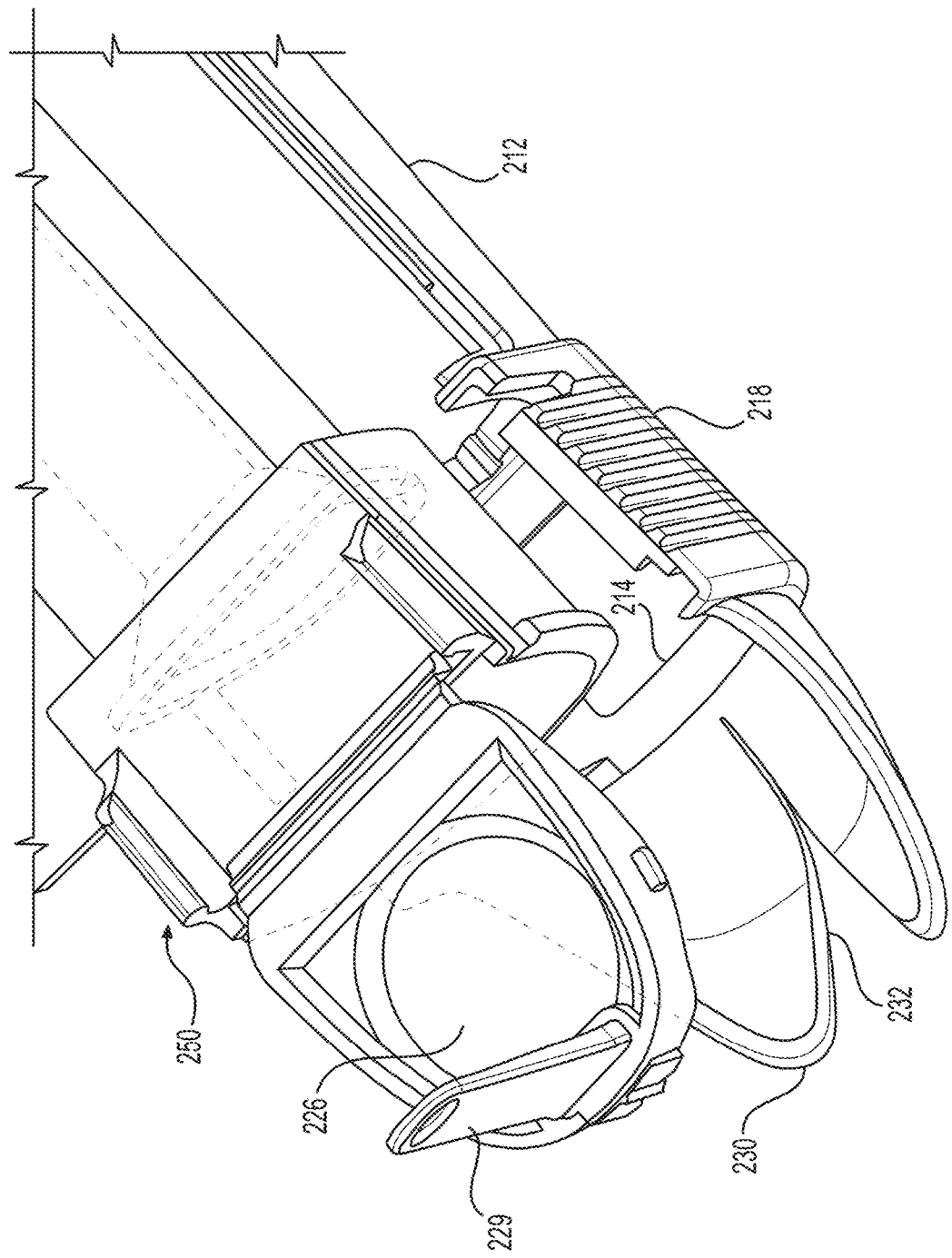
FIG. 32 is a top perspective view of the tick remover with a sweeper door above the scoop.

FIG. 32 is a top perspective view of the tick remover with a sweeper door above the scoop.

A top view detail of the scoop 230 and "V" slot 232 in FIG. 31 shows the top and the front portion of trap 220 or 250 in place. Trap 250 is being placed in or removed from the tool 210 as shown in FIG. 32. The sweeper door 260 as shown in FIG. 32 has outer edges 262 that increase in dimension from near the top 264 of the door to the bottom 266 of the door. The sides of the door have stops 265 that prevent over downward travel of the door.

The bottom of the door has an opening 268 which tightly holds an assembly 270 that includes an opening strip 272 nudgers 274.

Figure 33:
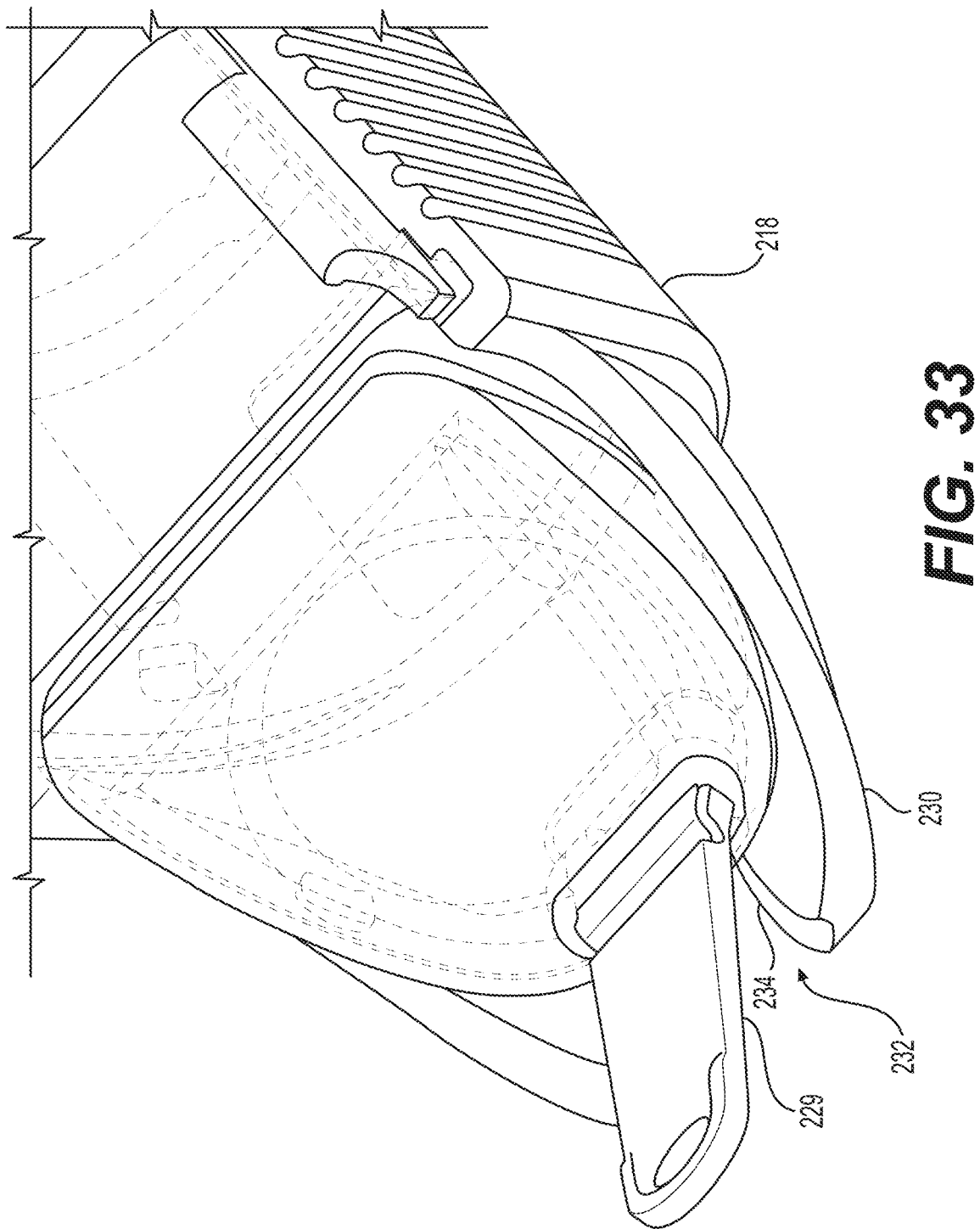
FIG. 33 is a top perspective view of the tick remover with a sweeper door being moved into the scoop.

FIG. 33 is a top perspective view of the tick remover with a sweeper door being moved into the scoop.

As shown in FIG. 33, as the door 220 closes the curved door sides sweep along the curved scoop 230. The nudger 228 leads the bottom edge 266 of the door 260 as it sweeps along the complementary curved scoop 230. The V-shaped slot 232 walls 234 are sloped and tapered to cooperate with the nudger 228 in lifting and centering a tick. A living hinge 222 on the lifting strip 219 allows the door 224 to be pulled open in any direction without affecting the operation of the nudger 228.

Figure 34:
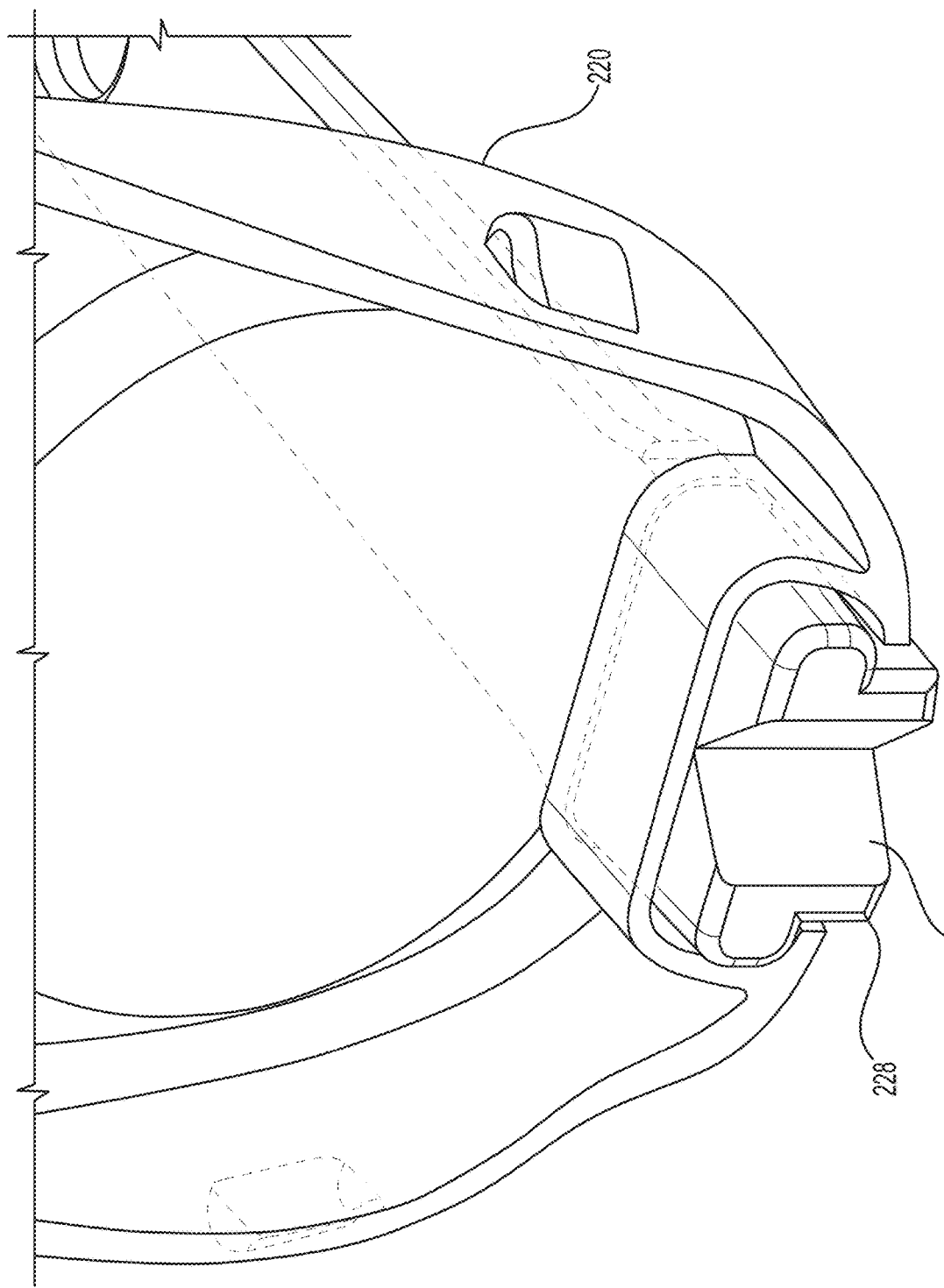
FIG. 34 is a perspective detail of an inside of the sweeper door having a nudge with a "V" notch.

FIG. 34 is a perspective detail of an inside of the sweeper door having a nudge with a "V" notch.

As shown in FIG. 34 on the inside of the door 220, the nudger 228 has a V-shaped notch 276 to aid in centering the tick and its legs that is being lifted and swept into the trap.

Figure 35:
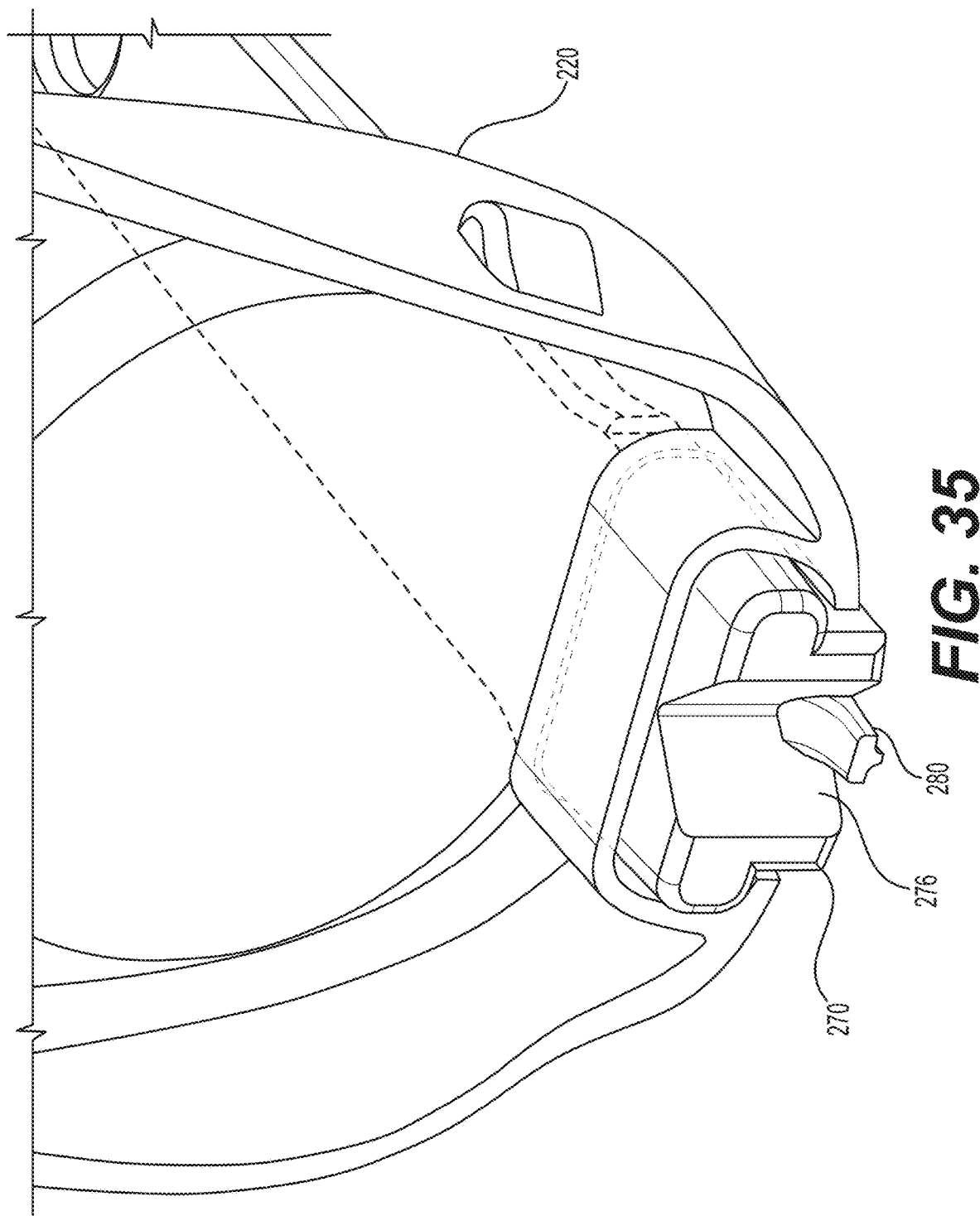
FIG. 35 is a perspective detail of an inside of the sweeper door having a nudge with a "V" notch with a flexible finger for engaging a tick in the scoop.

FIG. 35 is a perspective detail of an inside of the sweeper door having a nudge with a "V" notch with a flexible finger for engaging a tick in the scoop.

As shown in FIG. 35, below the nudger 228 a flexible finger 280 is mounted. The finger has an upper part 282 with a bottom surface 284 that rides on and is lifted by the sloped surfaces of the "V" notch to the inner surface of the scoop. A lower central extension 286 fits within the "V" notch until it is lifted by the "V" groove to lift the tick from the inner end of the groove.

Figure 36:
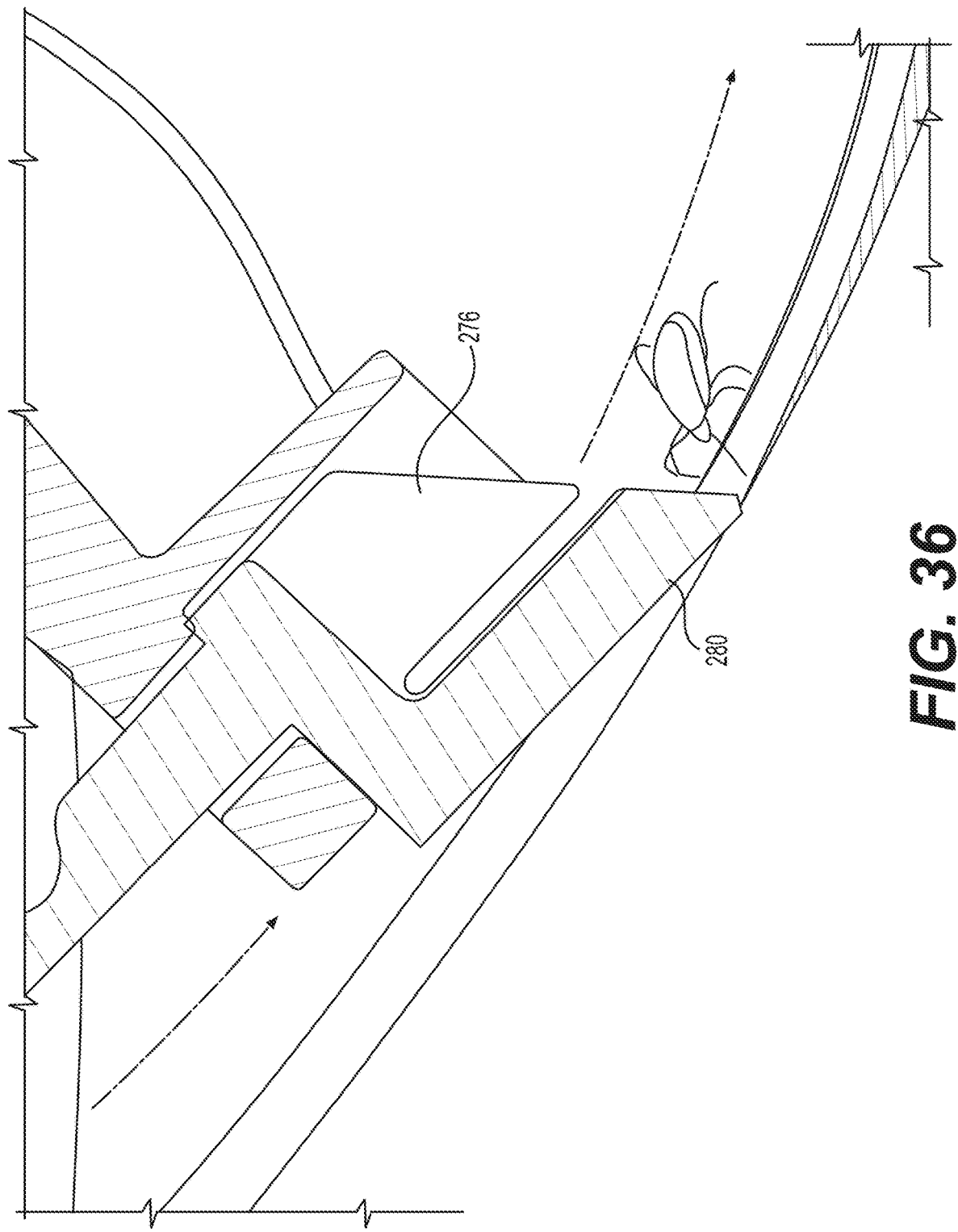
FIG. 36 is an enlarged perspective detail of a lower part of a hinged door with a V-shaped nudge and a flexible finger on a nudge pushing or following a tick along the notch in the scoop as it moves beneath a tick.

FIG. 36 is an enlarged perspective detail of a lower part of a hinged door with a V-shaped nudge and a flexible finger on a nudge pushing or following a tick along the notch in the scoop as it moves beneath a tick.

As shown in FIG. 36, the flexible ridge finger 284 and the nudger 274 have upward and rearward sloping leading walls to help lift the tick. The ridge finger flexes upwardly following the scoop into the trap. The nudger and the finger cooperate to sweep the tick upwardly into the trap.

One construction of the assembly 270 is shown with the nudger 274 being a main part 280 of the assembly 270. The lifting strip 272 and the nudger 274 and finger 280 are made of one molding and, together with the tightly holding rigid molding 290, form the door insert assembly 270.

The flexible finger 280 is extended forward of the nudger 290. The nudger is shown in two spaced parts 292, 294 to keep a lifted tick centered and moving toward the trap.

Figure 37:
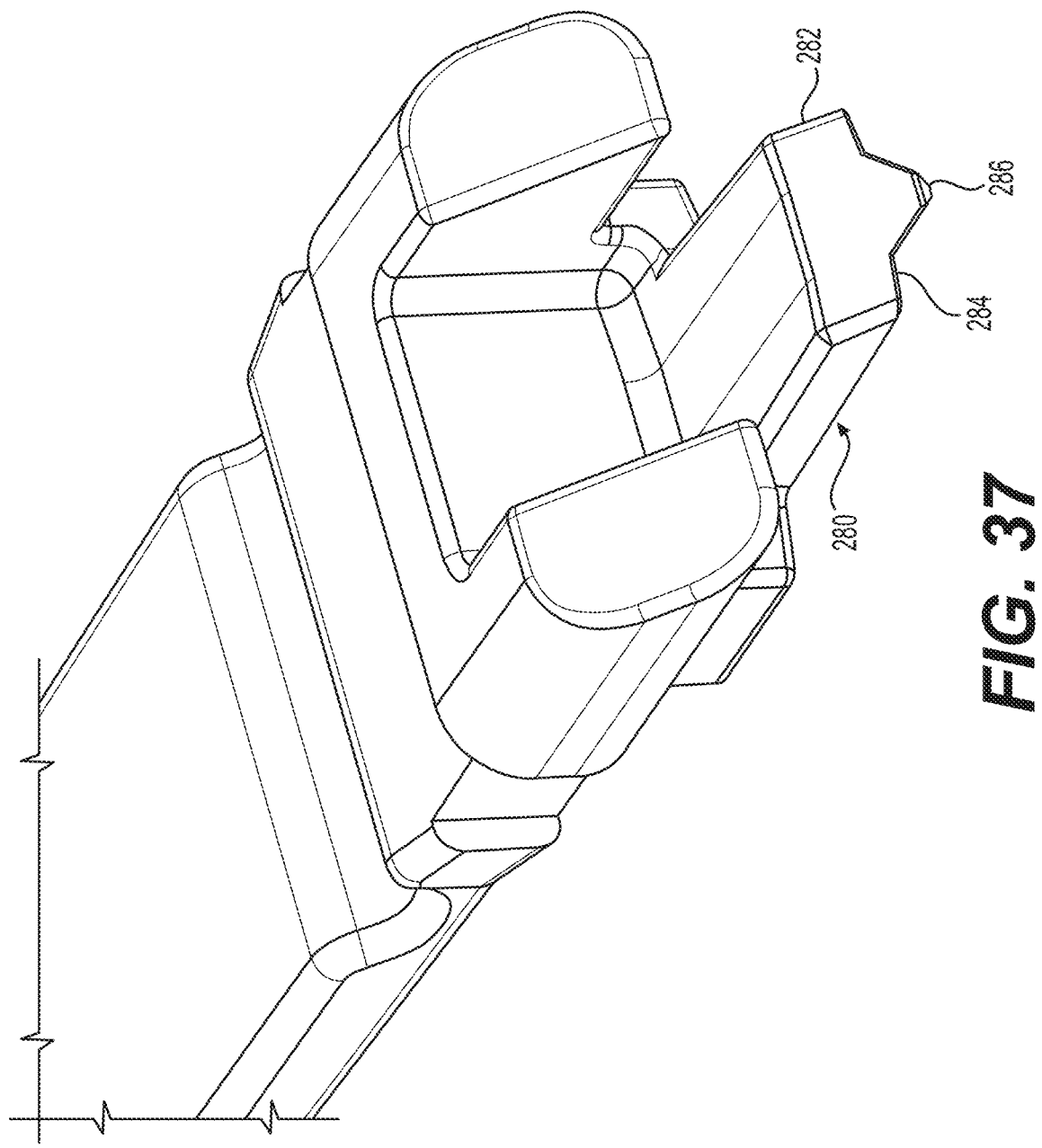
FIG. 37 is a detail of the nudger and flexible finger.

FIG. 37 is a detail of the nudger and flexible finger.

While the invention has been described with reference to specific embodiments, modifications and variations of the invention may be constructed without departing from the scope of the invention, which is defined in the following claims.

I claim:

1. Apparatus comprising:
   a tick remover and trap having
   a tick scoop with front and back, a V-shape notch in the scoop wide at the front of the scoop and narrowing toward the back of the scoop, a handle connected to the back of the scoop, a compartment in the handle at the back of the scoop, a trap positionable in the compartment for retaining one or more removed ticks, the trap having a top, sides, a bottom, a back and a front, a door having a top, sides and a bottom, a hinge connecting the top of the door and to the trap, the top of the door connected to the trap near an intersection of the top and the front of the trap, the bottom of the door contacting the bottom of the scoop near the narrowing of the V-shaped notch for urging a tick toward the front of the trap.

2. The apparatus of claim 1, wherein the scoop is curved and the bottom of the door is curved to sweep along the curved scoop and to move a tick toward the trap.

3. The apparatus of claim 2, wherein lower portions of the sides are curved inward toward the curved bottom of the door to sweep a tick toward the trap.

4. The apparatus of claim 1, wherein the front of the trap is open to receive one or more ticks removed by the scoop and the door.

5. The apparatus of claim 4, wherein the door closes the open front of the trap.

6. The apparatus of claim 1, wherein the door is held closed on the front of the trap by friction or cooperating snaps.

7. The apparatus of claim 1, wherein the door has extensions on the back of the door extending from the sides and the bottom of the door for sweeping the scoop and urging a tick toward the trap.

8. The apparatus of claim 1, wherein the V-shaped notch has upward sloping edges for lifting a tick as the scoop relatively moved under a tick.

9. The apparatus of claim 8, wherein the door has a nudger extending rearward from a center of the bottom of the door.

10. The apparatus of claim 9, wherein the nudger is V-shaped, narrowing inward toward a center of the nudger.

11. The apparatus of claim 9, further comprising a flexible finger extending below and forward of the nudger toward the trap.

12. The apparatus of claim 11, wherein the flexible finger has flat lower surfaces and a depending middle projection.

13. The apparatus of claim 12, wherein the flat lower surfaces engage the upward sloping edges of the V-shaped notch and the depending middle projection rides in the V-shaped notch until the sloping side edges near an apex of the V-shaped notch lift the flexible finger, which in turn gently lifts the tick, its head and rostrum proboscis from skin.

14. The apparatus of claim 1, wherein the handle has a hollow body and has a longitudinally hinged lid connected to the hollow body.

15. The apparatus of claim 14, wherein the hollow body is used for storage of auxiliary devices.

16. The apparatus of claim 14, wherein the trap is longitudinally extended, has longitudinally extended walls and extends into the hollow body beneath the lid.

17. The apparatus of claim 16, wherein the trap includes angular inward and rearward extending barriers extending into the trap from longitudinal walls spaced slightly inward from the front of the trap adapted for preventing ticks held deep in the trap from crawling outward beyond the barriers toward the front of the trap.

* * * * *